United States Patent [19]
Biel

[11] Patent Number: 6,048,359
[45] Date of Patent: Apr. 11, 2000

[54] SPATIAL ORIENTATION AND LIGHT SOURCES AND METHOD OF USING SAME FOR MEDICAL DIAGNOSIS AND PHOTODYNAMIC THERAPY

[75] Inventor: Merrill A. Biel, Mendota Heights, Minn.

[73] Assignee: Advanced Photodynamic Technologies, Inc., Mendota Heights, Minn.

[21] Appl. No.: 09/139,862

[22] Filed: Aug. 25, 1998

Related U.S. Application Data

[60] Provisional application No. 60/057,356, Aug. 25, 1997, abandoned.

[51] Int. Cl.⁷ .................................................... A61N 5/01
[52] U.S. Cl. .................................. 607/92; 607/89; 606/2
[58] Field of Search ................................ 606/1–3, 11, 13, 606/14; 607/88, 89, 92

[56] References Cited

U.S. PATENT DOCUMENTS

| | | |
|---|---|---|
| 4,200,110 | 4/1980 | Peterson et al. . |
| 4,281,645 | 8/1981 | Jöbsis . |
| 4,312,357 | 1/1982 | Andersson et al. . |
| 4,427,005 | 1/1984 | Tener . |
| 4,476,870 | 10/1984 | Peterson et al. . |
| 4,502,487 | 3/1985 | DuBrucq . |
| 4,515,165 | 5/1985 | Carroll . |
| 4,822,335 | 4/1989 | Kawai et al. ............................. 604/20 |
| 5,106,387 | 4/1992 | Kittrell et al. . |
| 5,163,935 | 11/1992 | Black et al. . |
| 5,349,954 | 9/1994 | Tiemann et al. . |
| 5,370,649 | 12/1994 | Gardetto et al. . |
| 5,413,108 | 5/1995 | Alfano . |
| 5,445,608 | 8/1995 | Chen et al. ............................. 604/20 |
| 5,460,182 | 10/1995 | Goodman et al. . |
| 5,483,961 | 1/1996 | Kelly et al. . |
| 5,728,090 | 3/1998 | Martin et al. ............................. 606/3 |
| 5,766,234 | 6/1998 | Chen et al. ............................. 607/92 |
| 5,782,896 | 7/1998 | Chen et al. ............................. 607/88 |
| 5,814,008 | 9/1998 | Chen et al. ............................. 604/21 |
| 5,827,186 | 10/1998 | Chen et al. ............................. 600/407 |

*Primary Examiner*—Linda C. M. Dvorak
*Assistant Examiner*—Roy Gibson
*Attorney, Agent, or Firm*—Larkin, Hoffman, Daly & Lindgren, Ltd.; John F. Klos

[57] ABSTRACT

A medical apparatus including implantable elongate probes for emitting diffused light energy within the interior of a tissue body to provide a uniform light dosage to the tissue body. In one particular embodiment, the probes may include a plurality of LEDs or VSCEL devices interspaced along the probe shaft. The invention further provides an planar or shaped alignment grid for aligning one or more probes within the tissue body.

24 Claims, 5 Drawing Sheets

SPATIAL ORIENTATION AND LIGHT SOURCES AND METHOD OF USING SAME FOR MEDICAL DIAGNOSIS AND PHOTODYNAMIC THERAPY

CROSS REFERENCE TO RELATED APPLICATION

This application claims the benefit of priority pursuant to 35 USC §119(e)(1) from the provisional patent application filed pursuant to 35 USC §111(b): as Serial No. 60/057356 on Aug. 25, 1997, now abandoned.

BACKGROUND OF THE INVENTION

1. Field of the Invention

This invention pertains to the implantation of light emitting devices into a tumor or other tissue body for treatment using light energy. More particularly this invention relates to a light probe incorporating LEDs or vertical cavity surface emitting lasers (VCSEL) and a structure for improving the placement of such probes in a tissue body. An alignment grid may be used to facilitate accurate placement of the light probe within the tissue body. Medical diagnostic situations and PDT treatment are environments which the present invention may be utilized. Photodynamic therapy (PDT) is a medical technology which uses light energy in combination with photosensitizing agents to treat or detect pathologies of living tissue, including cancer and microbiological pathogens. Once pre-sensitized by the photosensitizing agent, the cancerous or abnormal cells can be destroyed by irradiation with light of an appropriate wavelength or waveband corresponding to an absorbing wavelength of the agent, with less damage to normal tissue. This procedure has been clinically used to treat a variety of cancers and tumors. Because PDT may be selective in destroying abnormal cells that have absorbed more of the agent, it can successfully be used to destroy malignant tissue with less effect on surrounding benign tissue in the brain and other critical areas.

2. Brief Discussion of the Prior Art

Photodynamic therapy is a modality that involves the use of a photosensitizing agent and a specific wavelength of light to create oxygen radicals, resulting in the destruction of cancer cells, bacteria, viruses, or fungi. A PDT system consists of three principal components: a photosensitizing agent, a light source (typically a laser), and a light delivery means (typically optical fiber based). Two principal challenges for this emerging field of medicine are the development and validation of photosensitizer agents, and the development of reliable wavelength specific (laser) light sources at appropriate and convenient energy levels.

PDT entails the use of a photosensitizing agent that is relatively selectively concentrated in cancer cells or microbiological pathogen sites. Depending on the type of photosensitizer, it may be injected intravenously, ingested orally, or applied topically. After application of the photosensitizer, it is selectively retained by diseased tissue so that after a period of time, determined by the kinetics of the compound's distribution, there is more photosensitizer in the diseased tissue than in the normal tissue. The photosensitizer is then activated with a specific wavelength of light matching the absorption characteristics of the specific photosensitizer, typically using a laser. This results in tissue necrosis via several mechanisms including oxygen radical production as well as vascular shutdown to the diseased tissue. Because there is less photosensitizer in the adjacent normal tissue, only the diseased tissue necroses and the normal tissue is preserved when the correct light dose rate for that tissue is administered. The advantage of PDT over the other conventional modalities of surgery, radiation and chemotherapy is its relatively selective destruction of diseased tissue with normal tissue preservation.

One prior method of delivery of the light energy to the tissue site is by remote illumination through single or multiple optical fibers. The use of optical fibers allow for ease of manipulation and electrical isolation, important criteria in the surgical arena, as well as the possibility of delivery within the body by an endoscopic apparatus. The beam is typically modified by optical accessories on the distal end of the fiber optic cable to direct the energy in a manner appropriate to the treatment requirements. Limitations of the remote illumination of tissue from an optical fiber include irregular illumination and difficulty in obtaining consistent light dosage through out the tissue body (due to light absorbtion of the tissue).

SUMMARY OF THE INVENTION

The present invention is primarily intended to provide a laser medical apparatus for radiating a diseased tissue body with light issued from an implantable probe. The invention further provides a grid apparatus for aligning the probes in the tissue body. The grid apparatus promotes accuracy in the delivery of light doses within the tissue body and otherwise enhances the medical treatment. Still additional provisions of the present invention include a probe having one or more photodetectors for measuring light intensity within the tissue body. The light intensity information may be fed back to a controller for adjusting or otherwise optimizing the light delivery within the tissue body.

The present invention may be used in conjunction with or in relation to inventions disclosed in the following applications, filed on the same date concurrently herewith.

U.S. patent applications: M. Biel, Inventor:
  Method of Enhancing Photodynamic Therapy by Administering an Immunologic Adjuvant, Ser. No. 09/139, 861.
  Dye Treatment Solution and Photodynamic Therapy and Method of Using Same, Ser. No. 09/139,866.
  Rectangular Laser Irradiation Field Producing Apparatus for Medical Treatment, Ser. No. 09/139,480.
  Methylene Blue and Toluidene Blue Mediated Fluorescence Diagnosis of Cancer, Ser. No. 09/139,481.
  PCT Application: M. Biel, Inventor
  Treatment Device for Topical Photodynamic Therapy and Method of Making Same, PCT/US98/17589.

All documents within these applications are herein incorporated by reference in their entireties for all purposes.

DETAILED DESCRIPTION OF THE PREFERRED EMBODIMENTS

Figure 1:
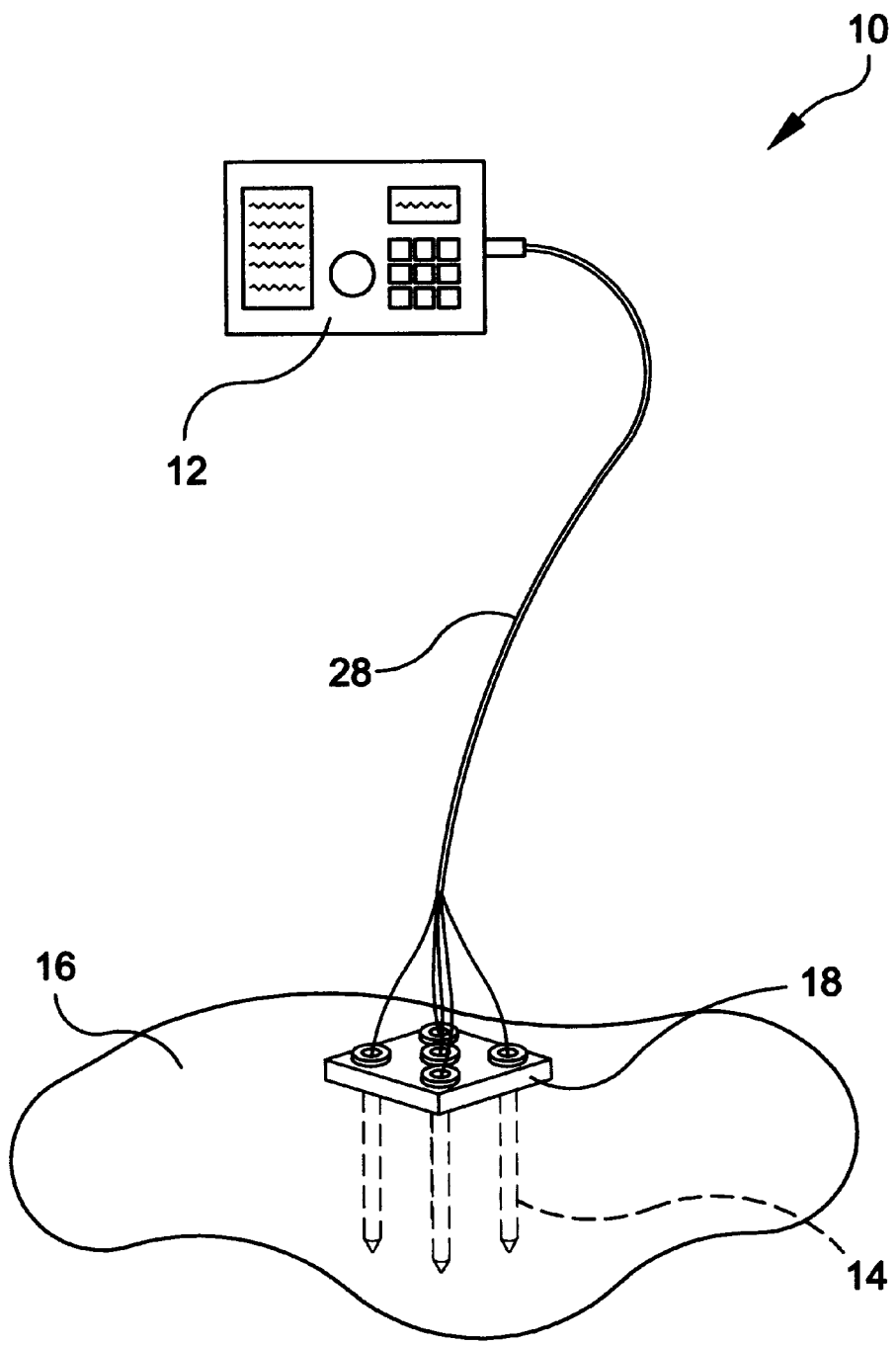
FIG. 1 is a schematic medical apparatus within which present invention may be utilized.

FIG. 1 illustrates a laser medical apparatus 10 incorporating features of the present invention. A power supply and controller 12 is electrically coupled to a plurality of probes 14 which are implantable within a tissue body 16. The medical apparatus 10 further includes an alignment grid 18 to position the probes 14 within the tissue body 16. Light may be emitted along the elongate shaft 20 of the probe 14 from light emitting sources 22. The light emitting sources 22 may include LEDs or vertical cavity surface emitting laser devices. The light emitting devices 22 may be imbedded within a polymeric or other material having light diffusive properties such that the emitted light is substantially diffused and uniform around the elongate shaft 20. Individual probes 14 may be rigid or substantially rigid and be insertable or implantable within the tissue body 16. As discussed further herein, the individual probes 14 may inserted through a metal sheath 19 or may be self-injectable by having a sharpened portion 21. A method of use of the apparatus 10 would comprise the steps of: identifying a tissue site 16; determining whether or not a photosensitizing compound would be utilized for photodynamic light therapy; administering the photosensitizing compound if required; positioning the alignment grid 18 above the tissue body 16; implanting each of a plurality of probes 14 by passing each probe 14 through an associated aperture 24 of the alignment grid 18 and into the tissue body 16; activating the light sources 22 of the probes 14; and maintaining the light probes 14 in place within the tissue body 16 until a desired light dose is achieved. The probes 14 may have photodetector devices 26 incorporated therein such that additional steps for the method of use may include monitoring the light intensity detected by the photodetectors 26; feeding the light intensity information back to the controller 12; and adjusting the light energy accordingly. Light intensity information may further be used to generate 2D or 3D mapping of the tissue body 16.

Figure 2:
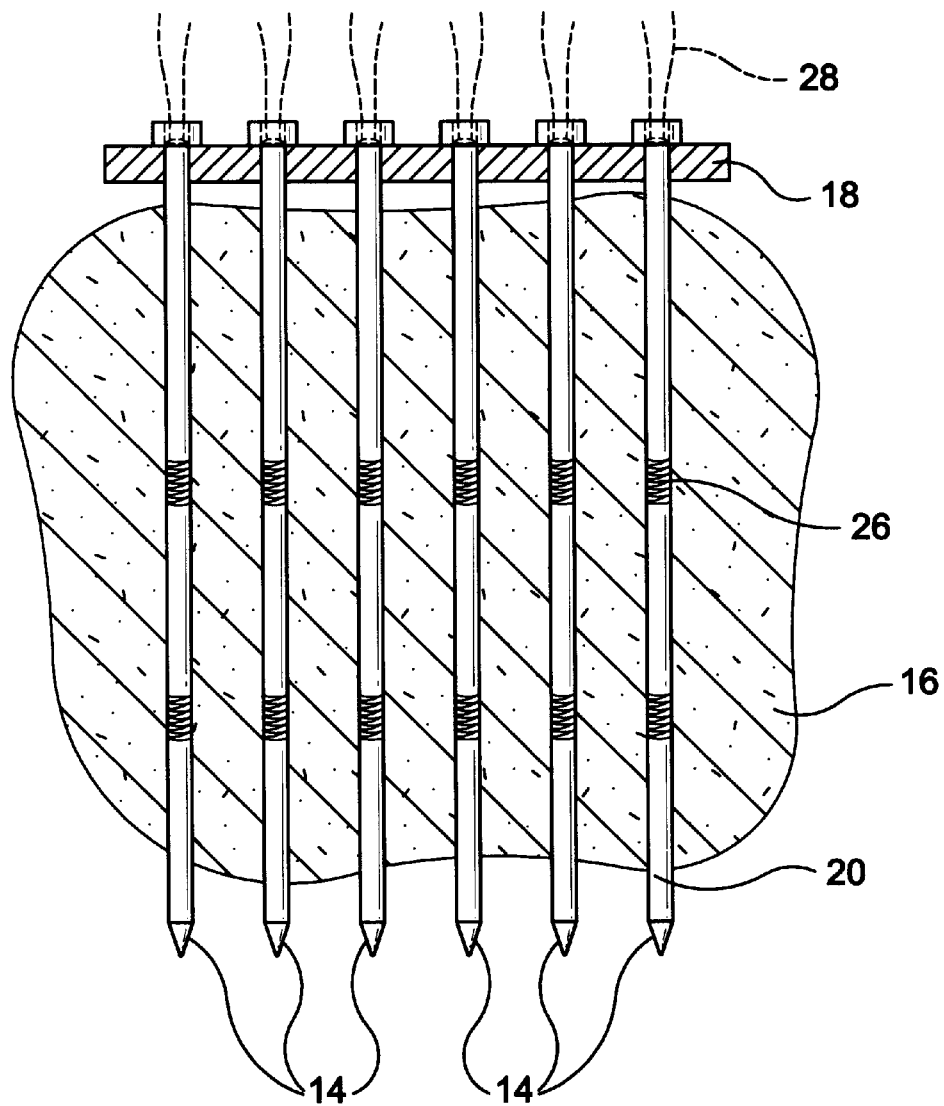
FIG. 2 is an elevational view of a plurality of light emitting probes implanted within a tissue body and aligned with an alignment grid.

FIG. 2 illustrates a side elevational view of the alignment grid 18 and plurality of probes 14 implanted within a tissue body 16, each probe 14 being parallely aligned by the alignment grid 18. The probes 14 may be passed (with the sharpened portion 21 first) through aligned probe apertures 24 in the alignment grid 18 and into the tissue body 16 by perforation. One or more probe 14 may be operatively coupled to the controller 12 through connections 28 (electrical, fiber optic, etc.) to provide light intensity information from photodetectors 26.

Figure 3:
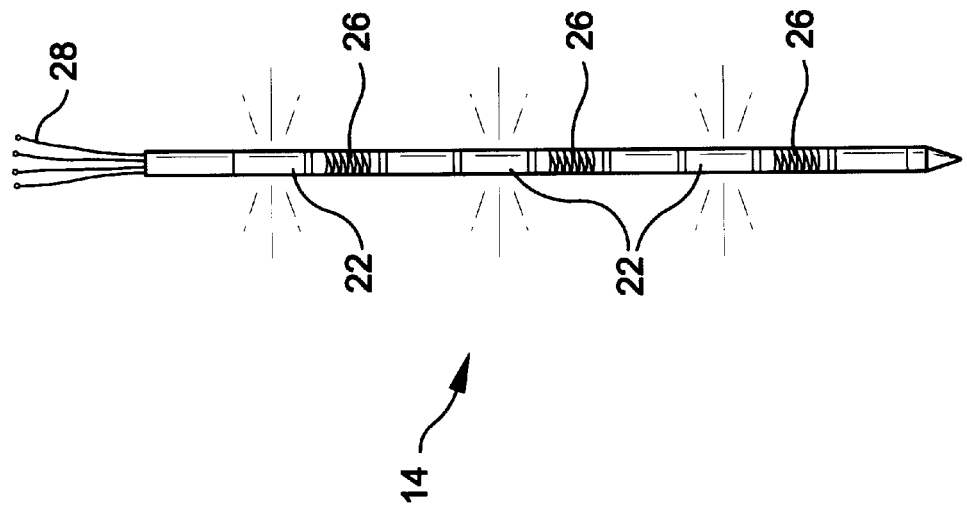
FIG. 3 is an elevational view of a first embodiment of an implantable probe.

FIG. 3 illustrates an embodiment of an implantable probe 14 for insertion within the tissue body 16. The probe 14 includes an elongate shaft 20 and one or more light emitting devices 22. The probe 14 further includes a sharpened portion 21 for facilitating the injection of the probe 16 into the tissue body 16. The light emitting devices 22 may include LEDs or vertical cavity surface emitting laser devices (VCSELS). A diffusive coating or diffusion layer encompasses the light emitting devices 22 and promotes uniform and consistent light diffusion into the tissue body 16. The light emitting devices 22 are powered by the controller 12 and are operatively coupled by connectors 28. The light intensity of the light emitting devices 22 may be controlled by the controller 12. Furthermore, the intensity of the light from the light emitting devices along the elongate shaft 20 of a probe 14 may be variable and controllable. The physical dimensions of a probe 14 may be approximately 0.5 to 6.0 inches in length, with a 0.2 to 2.0 mm diameter. The probes 14 may be formed of flexible or rigid silicon or other plastic. The probe may be coated with a diffusive material or layer to facilitate the uniform diffusion of light from the light emitting devices 22. The light emitting devices 22 are fixedly secured along the probe shaft 20.

Figure 4:
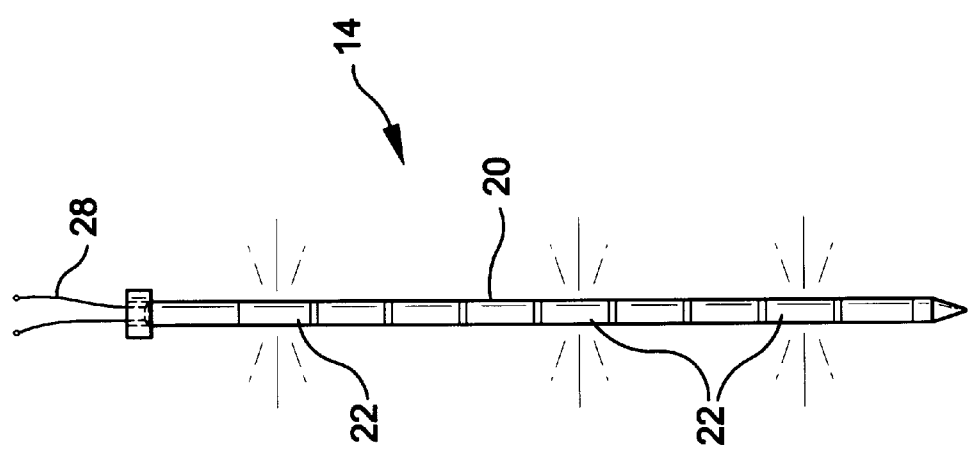
FIG. 4 is an elevational view of a second embodiment of an implantable probe including photodetectors.

FIG. 4 illustrates another embodiment of an implantable probe 14 according to the present invention. Probe 14 includes one ore more light emitting devices 22 and one or more photodetector devices 26 for measuring light intensity. When the probe 14 is implanted, the photodetectors 26 may be used to measure the light intensity provided to the tissue body 16 from the light emitting devices 22. Information provided by the photodetectors 26 may be fed back to the controller 12 via connectors 28. The light intensity information may be used to generate 2D or 3D mappings of the tissue body 16 as readily appreciated by one skilled in the art of medical imaging.

Figure 7:
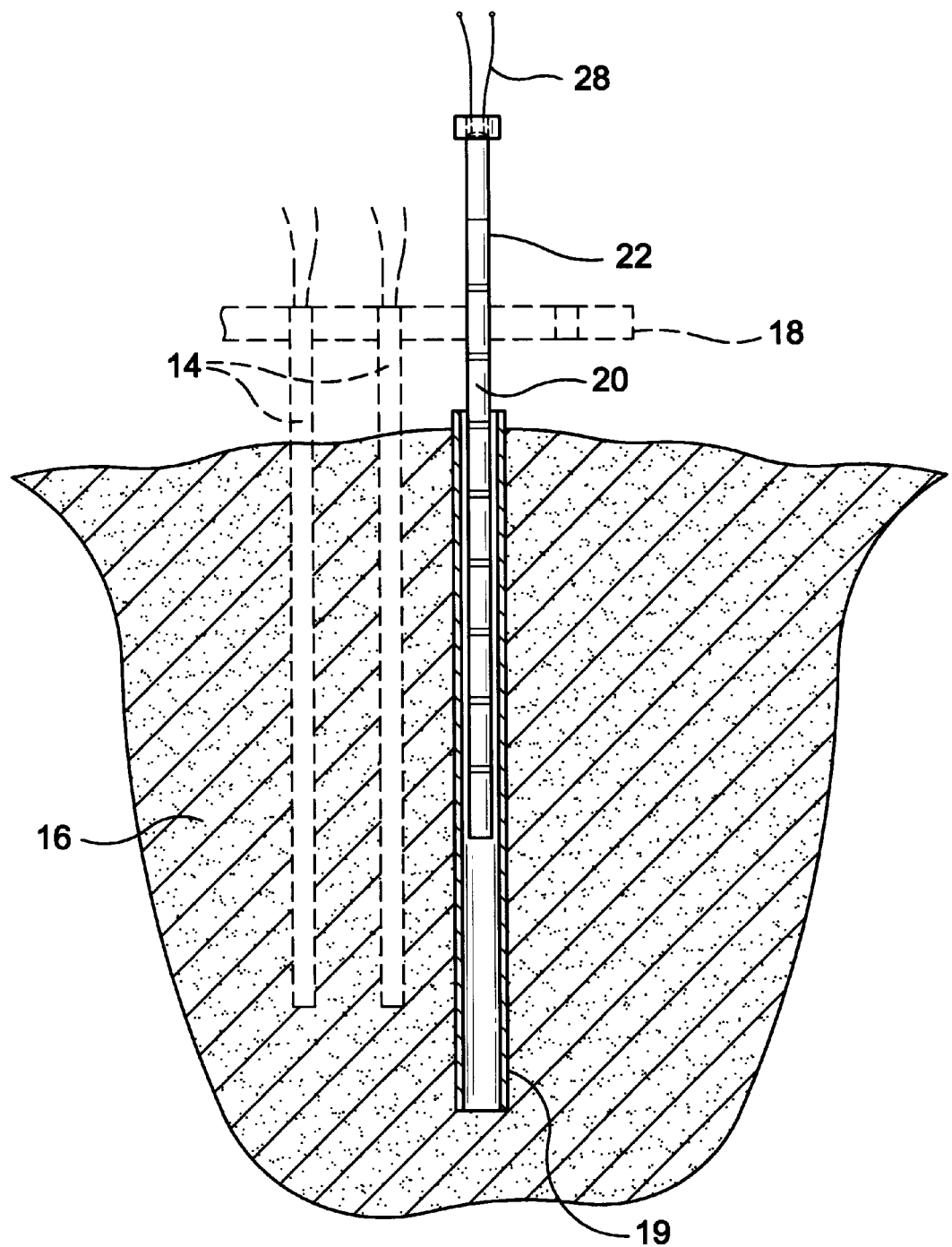
FIG. 7 is a side elevation view of another embodiment of an implanted probe and an insertion sheath.

Implantable probe 14 may include a rigid elongate shaft 20 having a sharpened portion 21 to facilitate injection into the tissue body 16. As illustrated in FIG. 7, implantable probe 14 may alternatively by inserted by passing a probe 14 with or without a sharpened portion 21 through a metal sheath 19 previously or simultaneously positioned within the tissue body 16. The implantable probe 14 is formed of a generally rigid polymeric material, though a pliant or non-rigid probe 14 may also be practicable. The implantable probe 14 may be formed of an inherently diffusive polymeric material or may included a diffusive layer or coating. The light emitting devices 22 may be fixedly secured to the probe 14 through an embedment procedure or adhesive secured thereto.

Figure 6:
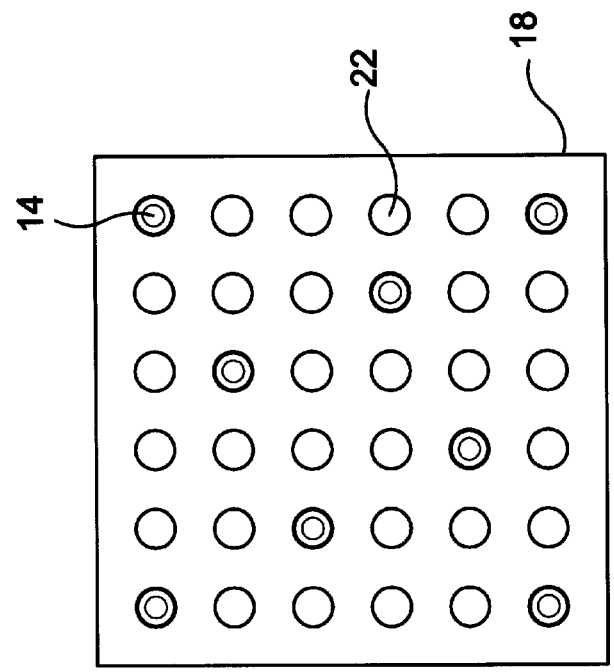
FIG. 6 is a top plan view of a second embodiment of an alignment grid for receiving and aligning a plurality of implantable probes.
Figure 5:
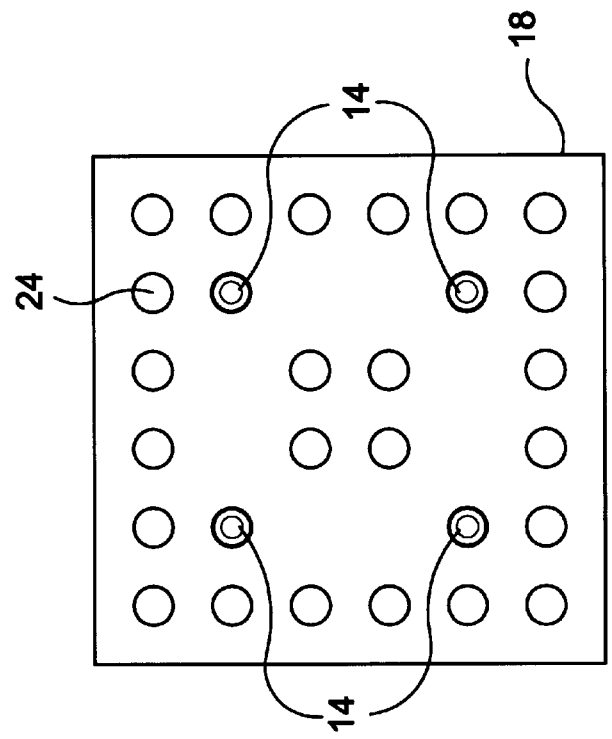
FIG. 5 is a top plan view of a first embodiment of an alignment grid for receiving and aligning a plurality of implantable probes.

Two alignment grids 18 are illustrated in FIGS. 5 and 6. Each alignment grid 18 is a relatively rigid body having a plurality of interspaced apertures 24 which are sized to permit the probes 14 to pass therethrough. The particularly spacing between apertures 24 may vary. In use, the grid 18 can maintain one or more probes 14 in substantially parallel alignment within the tissue body 16. The alignment grids 18 of FIGS. 5 and 6 are depicted as generally planar in form, though alternative, a curved or configured alignment grid (not shown) may also be practicable. The alignment grid 18 may be shaped with reference to the particular tissue site of interest.

A method of use of the apparatus according to the present invention includes the steps of identifying a tissue body 16 for treatment, positioning the alignment grid 18 above the tissue body 16, passing one or more probes 14 through the alignment grid 18 and into the tissue body 16, activating the light emitting devices 22 of the one or more probes 14 to provide light energy within the tissue body 16, detecting the light intensity within the tissue body 16 with photodetectors 26 on the one or more probes 14, adjusting the light intensity, if desired, and maintaining the one or more probes 14 in place to providing a light dose to the tissue body 16.

While the preferred embodiments of the above apparatus have been described in detail with reference to the attached drawing figures, it is understood that various changes and adaptations may be made without departing from the spirit and scope of the appended claims.

What is claimed is:

1. An implantable probe for insertion within a tissue body for a predetermined time, said probe comprising:

an elongate probe shaft;

a plurality of light emitting devices secured to said elongate probe shaft for emitting light within the tissue body, said light having a light intensity, said plurality of light emitting devices delivering a light energy dose depending on said light intensity and the predetermined time; and an alignment grid having at least one aperture for receiving the elongate probe shaft therethrough.

2. The implantable probe according to claim 1 wherein the elongate probe shaft is formed of a polymeric diffusive material for diffusing the light emitted from the light emitting devices.

3. The implantable probe according to claim 2 further comprising:

one or more photodetectors secured to the elongate probe shaft, said one or more photodetectors capable of providing information relating to the light intensity.

4. The implantable probe according to claim 1 wherein the light emitted from the plurality of light emitting devices is variable.

5. The implantable probe according to claim 1 wherein the elongate probe shaft includes a sharpened end portion.

6. The implantable probe according to claim 1 wherein the light emitting devices may be selected from among the group including: LED devices and vertical cavity surface emitting lasers.

7. An implantable probe for insertion within a tissue body for a predetermined time, said probe comprising:

an elongate probe shaft;

a plurality of light emitting devices secured to said elongate probe shaft for emitting light within the tissue body, said right having a light intensity, said plurality of light emitting devices delivering a light energy dose depending on said light intensity and the predetermined time, wherein the plurality of light emitting devices and the one or more photodetectors are alternately spaced along the elongate probe shaft.

8. The implantable probe according to claim 7 wherein the light emitted from each of the plurality of light emitting devices is variable.

9. A medical apparatus for delivering light within a tissue body, comprising:

a controller having a power supply;

a plurality of implantable probes for inserting within the tissue body, each probe having an elongate probe shaft and one or more light emitting devices secured to said elongate probe shaft; said one or more light emitting devices operatively coupled to the power supply of the controller for emitting light within the tissue body when implanted within the tissue body, said light having a light intensity, said one or more light emitting devices delivering a light energy dose depending on said light intensity and a predetermined time during which the implantable probes are within the tissue body; and an alignment structure having a plurality of interspaced apertures sized to allow the implantable probes to pass therethrough when positioned at the tissue body, said alignment structure capable of receiving and aligning a plurality of implantable probes.

10. The medical apparatus according to claim 9, wherein the implantable probe further includes one or more photodetectors for providing light intensity information, said photodetectors being operatively coupled to the controller to convey said light intensity information.

11. The medical apparatus according to claim 10 wherein the controller receives the light intensity information and adjusts the light emitted from the probe.

12. The medical apparatus according to claim 9 wherein the implantable probe includes a polymeric diffusive material for diffusing the light emitted from the light emitting devices.

13. The medical apparatus according to claim 12 wherein light delivered within the tissue body is substantially uniform throughout the tissue body.

14. The medical apparatus according to claim 9, wherein the light emitted by the one or more light emitting devices of the probe is adjustable by the controller.

15. The medical apparatus according to claim 9 wherein the plurality of interspaced apertures of the alignment structure maintains an implanted plurality of probes within the tissue body in substantially parallel alignment.

16. The medical apparatus according to claim 9 wherein the alignment structure is substantially planar in form.

17. The medical apparatus according to claim 9 wherein the alignment structure is shaped with regard to a physical characteristic of the tissue body.

18. The medical apparatus according to claim 9 wherein the controller receives the light intensity information and generates a map of the tissue body based upon the light intensity information.

19. The medical apparatus according to claim 9 wherein the one or more light emitting devices may be selected from among the group including: LED devices and vertical cavity surface emitting lasers.

20. The medical apparatus according to claim 9 further comprising:

a photosensitizing compound which is capable of being delivered to the tissue body.

21. The medical apparatus according to claim 20 wherein the one or more light emitting devices is selected with regard to the photosensitizing compound.

22. A method of treating tissue comprising the steps of:

identifying a tissue body;

placing an alignment structure having a plurality of interspaced apertures therethrough proximate the tissue body;

passing a plurality of elongate probes through the plurality of interspaced apertures and into the tissue body, said elongate probes each having one or more light emitting devices for emitting light at a predetermined intensity;

maintaining the elongate probes in place within the tissue body for a predetermined time period; and removing the elongate probes and alignment structure away from the tissue body after the predetermined time period.

23. The method of treating tissue according to claim 22 wherein a plurality of the elongate probes are inserted into the tissue body to provide a substantially uniform light density within the tissue body.

24. The method of treating tissue according to claim 22 comprising the additional steps of:

administering a photosensitizing compound to the tissue body; and selecting the particular light emitting device with regard to the photosensitizing compound.

* * * * *